US007625861B2

(12) United States Patent
Konfino et al.

(10) Patent No.: US 7,625,861 B2
(45) Date of Patent: Dec. 1, 2009

(54) COPOLYMER-1 IMPROVEMENTS IN COMPOSITIONS OF COPOLYMERS

(75) Inventors: Eliezer Konfino, Ramat Gan (IL); Michael Sela, Rehovot (IL); Dvora Teitelbaum, Rehovot (IL); Ruth Arnon, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 484 days.

(21) Appl. No.: 11/656,505

(22) Filed: Jan. 23, 2007

(65) Prior Publication Data
US 2007/0117757 A1 May 24, 2007

Related U.S. Application Data

(63) Continuation of application No. 11/098,432, filed on Apr. 5, 2005, now Pat. No. 7,199,098, which is a continuation of application No. 10/615,865, filed on Jul. 10, 2003, now Pat. No. 6,939,539, which is a continuation of application No. 10/014,477, filed on Dec. 14, 2001, now Pat. No. 6,620,847, which is a continuation of application No. 09/510,466, filed on Feb. 22, 2000, now Pat. No. 6,362,161, which is a continuation of application No. 09/032,334, filed on Feb. 27, 1998, now Pat. No. 6,048,898, which is a continuation of application No. 08/447,146, filed on May 22, 1995, now Pat. No. 5,800,808, which is a continuation-in-part of application No. 08/344,248, filed on Nov. 23, 1994, now abandoned, which is a continuation of application No. 08/248,037, filed on May 24, 1994, now abandoned.

(51) Int. Cl.
A61K 38/00 (2006.01)
A61K 31/195 (2006.01)
(52) U.S. Cl. .............................. 514/2; 514/12; 514/561
(58) Field of Classification Search ............... 514/2, 514/12, 561
See application file for complete search history.

(56) References Cited

U.S. PATENT DOCUMENTS

| | | | |
|---|---|---|---|
| 3,849,550 A | 11/1974 | Teitelbaum et al. ........... 424/78 |
| 4,444,760 A | 4/1984 | Thomas, Jr. | |
| 4,594,409 A | 6/1986 | Hayashii et al. | |
| 4,828,706 A | 5/1989 | Eddleman | |
| 5,800,808 A | 9/1998 | Konfino et al. ........... 424/78.08 |
| 5,981,589 A | 11/1999 | Konfino et al. .............. 514/561 |
| 6,048,898 A | 4/2000 | Konfino et al. .............. 514/561 |
| 6,054,430 A | 4/2000 | Konfino et al. ................ 514/12 |
| 6,214,791 B1 | 4/2001 | Arnon et al. .................... 514/2 |
| 6,342,476 B1 | 1/2002 | Konfino et al. ................. 514/2 |
| 6,362,161 B1 | 3/2002 | Konfino et al. ................. 514/2 |
| 6,620,847 B2 | 9/2003 | Konfino et al. .............. 514/561 |
| 6,936,539 B2 | 8/2005 | Yin et al. ..................... 438/689 |
| 7,199,098 B2 * | 4/2007 | Konfino et al. ................. 514/2 |
| 2005/0159336 A1 | 7/2005 | Eisenbach-Schwartz et al. .......................... 514/2 |

FOREIGN PATENT DOCUMENTS

| | | |
|---|---|---|
| DE | 39 30 733 | 3/1991 |
| EP | 0 378 246 | 7/1990 |
| EP | 0 383 620 | 8/1990 |
| RU | 1690368 A1 | 8/1995 |
| RU | 1469826 A1 | 11/1995 |
| SU | 1182051 | 9/1985 |
| SU | 1664845 | 7/1991 |

OTHER PUBLICATIONS

D. Titelbaum et al., article entited "Experiment in Treating Multiple Sclerosis with Copolymer 1 (COP )", Harefuah, Journal of the Israel Medical Association, vol. CXVI, No. 9, May 1, 1989, Jerusalem (full translation).
Borenstein et al., New Engl J Med, Aug. 13, 1987, vol. 317 (No. 7), pp. 408-414.
Borenstein et al., Neurology, Jul. 1988, vol. 38 (No. 7 Supl 2), pp. 66-69.
Borenstein et al., Neurology, Jul. 1988, vol. 38 (No. 7 Supl 2), pp. 80-81.
Johnson et al., Neurobiology, Jul. 1995, vol. 45 (No. 7), pp. 1268-1276.
Bornstein et al., Neurobiology, Apr. 1991, vol. 41 (No. 4), pp. 533-539.
Borenstein, Hosp Pract (Off Ed). May 15, 1992; vol. 27 (No. 5):135-138, 141-142, 145-158.
Korczyn et al., J Neurol., Apr. 1996; 243 (4 Suppl 1): pp. S23-S26.
D. Teitelbaum et al., "Dose-Response Studies on Experimental Allergic Encephalomyelitis Suppression by COP 1," *Israel Journal of Medical Sciences*, vol. 10, No. 9, Sep. 1974, pp. 1172-1173.
D. Teitelbaum et al., "Suppression of Experimental Allergic Encephalomyelitis by a Synthetic Polypeptide", *Eur. J. Immunol.*, 1971, 1, 242-248.
D. Teitelbaum et al., "Protection Against Experimental Allergic Encephalomyelitis", *Nature*, 1972, 240, pp. 564-566.
C. Webb et al., "Further Studies on the Suppression of Experimental Allergic Encephalomyelitis by Synthetic Copolymer", *Israel J. Med. Sci.*, 1972, 8, pp. 656-657.
R. Arnon et al., "Suppression of Experimental Allergic Encephalomyelitis by a Synthetic Copolymer Immunological Cross Reactive with Basic Encephalitogen", *Israel J. Med. Sci.*, 1972 8, pp. 1759-1760.
D. Teitelbaum et al., "Suppression of Experimental Allergic Encephalomyelitis with Basic Polymers", *Eur. J. Immunol.*, 1973, 3, pp. 273-279.
C. Webb et al., "In vivo and in Vitro Immunological cross-reactions between Basic Encephalitogen and Synthetic Basic Polypeptides Capable of Suppressing Experimental Allergic Encephalomyelitis", *Eur. J. Immunol*, 3, pp. 279-286, 1973.

(Continued)

Primary Examiner—Raymond J Henley, III
(74) Attorney, Agent, or Firm—Kenyon & Kenyon LLP

(57) ABSTRACT

The present invention relates to an improved composition of copolymer-1 comprising copolymer-1 substantially free of species having a molecular weight of over 40 kilodaltons.

11 Claims, 2 Drawing Sheets

OTHER PUBLICATIONS

D. Teitelbaum et al., "Suppression of Experimental Allergic Encephalomyelitis in Rhesus Monkeys by a Synthetic Basic Copolymer", Clin. Immunol. Immunopath, 1974, 3, pp. 256-262.

D. Teitelbaum et al., "Dose-response Studies on Experimental Allergic Encephalomyelitis Suppression by COP-1", *Israel J. Med. Sci.*, 1974, 10, pp. 1172-1173.

C. Webb et al., "Suppression of Experimental Allergic Encephalomyelitis in Rhesus Monkeys by a Synthetic Basic Copolymer", *Isr. J. Med. Sci.*, 1975, 11, pp. 1388 (abstract).

C. Webb et al., "Molecular Requirements Involved in Suppression of EAE by Synthetic Basic Copolymers of Amino Acids", *Immunochemistry*, 1976, 13, pp. 333-337.

O. Abramsky et al., "Effect of a Synthetic Polypeptide (COP-1) on Patients with Multiple Sclerosis and with Acute Disseminated Encephalomyelitis", *J. Neurol. Sci.*, 1977, 31, pp. 433-438.

D. Teitelbaum et al., "Suppression of Experimental Allergic Encephalomyelitis in Baboons by COP-1." *Israel J. Med. Sci.*, 1977, 13, 1038 (abstract).

M. Sela et al., "Experimental Allergic Encephalomyelitis in Menarini Series on Immunopathology, vol. 1, First Symposium of Organ Specific Autoimmunity", Cremona, Italy, Jun. 1977, Miescher P.A. ed., pp. 9-21, Schwabe Co., Basel, (1978).

R. Arnon et al., "Suppression of EAE in Baboons by a Synthetic Polymer of Amino Acids", *Neurology*, 1978, 28, 336 (abstract).

E.C. Alvord et al., "Myelin Basic Protein Treatment of Experimental Allergic Encephalomyelitis in Monkeys", *Ann. Neurol*, 1979, 6, pp. 469-473.

A. B. Keith et al., "The Effect of COP-1, a Synthetic Polypeptide, on Chronic Relapsing Experimental Allergic Encephalomyelitis in Guinea Pigs", *J. Neurol. Sci.*, 1979, 42, pp. 267-274.

Z. Lando et al., "Effect of Cyclophosphamide on Suppressor Cell Activity in Mice Unresponsive to EAE", *J. Immunol*, 1979, 123, pp. 2156-2160 (abstract).

Z. Lando et al., "Experimental Allergic Encephalomyelitis in Mice-Suppression and Prevention with COP-1", *Israel J. Med. Sci.*, 1979, 15, pp. 868-869 (abstract).

D. Teitelbaum et al., "Blocking of Sensitization to Encephalitogenic Basic Protein in Vitro by Synthetic Basic Copolymer (COP-1)," in *Cell biology and Immunology of Leukocyte Function*, Academic Press, New York, 1979, pp. 681-685.

D. Teitelbaum, "Suppression of Experimental Allergic Encephalomyelitis with a Synthetic Copolymer-relevance to Multiple Sclerosis", in *Humoral Immunity in Neurological Diseases*, Karcher D., Lowenthal A. & Strosberg A.D. eds. Plenum Publishing Corp., 1979, pp. 609-613.

R. Arnon et al., "Desensitization of Experimental Allergic Encephalomyelitis with Synthetic Peptide Analogues" in *The Suppression of Experimental Allergic Encephalomyelitis and Multiple Sclerosis*, Academic Press, New York, 1980 pp. 105-107.

R. Arnon, "A Synthetic Copolymer of Amino Adds in a Clinical Trail for MS Therapy" in Progress in *Multiple Sclerosis Research*, Bauer, Ritter, eds. Springer Verlag N.Y., 1980 pp. 416-418.

M. B. Bornstein et al, "Treatment of Multiple Sclerosis with a Synthetic Polypeptide: Preliminary results.", *Trans. Am. Neurol. Assoc.*, 1980, 105, pp. 348-350.

M. B. Bornstein et al., "Treatment of Multiple Sclerosis with a Synthetic Polypeptide: preliminary results", *Ann. Neuro.*, 1980, 8, pp. 117 (abstract).

J. R. McDermott et al., "Antigen-induced Suppression of Experimental Allergic Neuritis in the Guinea Pig.", *J. Neurol. Sci.*, 1980, 46, pp. 137-143.

R. Arnon, "Experimental Allergic Encephalomyelitis-Susceptibility and Suppression", *Immunological Rev.*, 1981, 55, pp. 5-30.

M. B. Bornstein et al., "Multiple Sclerosis: Trial of a Synthetic Polypeptide", *Ann. Neurol.*, 1982, 11, pp. 317-319.

C. G. Brosnan et al., "The Response of Normal Human Lymphocytes to Copolymer-1." *J. Neuropath. Exp. Neurol.*, 1983, 42, pp. 356 (abstract).

R. P. Lisak et al., "Effect of Treatment with Copolymer 1 (COP-1) on the in Vivo and in Vitro Manifestations of Experimental Allergic Encephalomyelitis (EAE)", J. Neurol. Sci., 1983, 62, 281-293.

M. B. Bornstein et al., "Clinical Trials of Copolymer 1 in Multiple Sclerosis", *Ann. N.Y. Acad. Sci*, (USA), 1984, pp. 366-372.

M. B. Bornstein et al., "Clinical Trials of a Synthetic Polypeptide (Copolymer 1) for the Treatment of Multiple Sclerosis" in R.E. Gonsett et al., eds. *Immunological and clinical aspects of multiple sclerosis*, 1984, pp. 144-150.

C. F. Brosnan et al., "Copolymer 1: Effect on Normal Human Lymphocytes", *Ann. N.Y. Acad. Sci.* (USA), 1984, 436, pp. 498-499.

J. Burns et al., "Human Cellular Immune Response in Vitro to Copolymer 1 and Myelin Basic Protein (MBP)", *Neurology*, 1985, 35, (suppl 1), 170 (abstract).

C. F. Brosnan, et al., "Immunogenic potentials of copolymer 1 in normal human lymphocytes" *Neurology*, 1985, 35, pp. 1754-1759.

M. B. Bornstein et al., "Multiple Sclerosis: Clinical Trials of a Synthetic Polypeptide, Copolymer I.", *Neurology*, 1985, 35, (suppl 1), p. 103 (abstract).

D. Teitelbaum et al., "Monoclonal antibodies to Myelin Basic Protein Cross React with a Synthetic EAE Suppressive Copolymer, COP 1.", *Proc. 7th European Immunology Meeting*, Jerusalem, 1985 (abstract).

J. Burns et al., "Human Cellular Immune Response to Copolymer 1 and Myelin Basic Protein." *Neurology*, 1986, 36, pp. 92-94.

M. B. Bornstein, "COP-1 may be Beneficial for Patients with Exacerbating-remitting Form of Multiple Sclerosis", *Adv. Ther.* (USA), 1987, 4, p. 206 (Abstract).

H. L. Winer, "COP-1 Therapy for Multiple Sclerosis", *New England Journal of Medicine*, 1987, 317, pp. 442-444.

R. Arnon et al., "Suppression of Demyelinating Diseases by Synthetic Copolymers", from: *A multidisciplinary approach to myelin disease* G. Serlupi Crescenzi, ed. Plenum Publishing Corporation, 1988, pp. 243-250.

M. B. Bornstein et al., "Pilot Trial of COP-1 in Chronic Progressive Multiple Sclerosis: Preliminary Report", *Elsevier Science Publisher*, 1989, pp. 225-232; Conference "The International Multiple Sclerosis Conference: an update on Multiple Sclerosis" Roma (Italy), Sep. 15-17, 1988.

E. Grgacic et al., "Cell-mediated Immune Response to Copolymer 1 in Multiple Sclerosis Measured by the Macrophage Procoagulant Activity Assay", *Int. Immunol*, 1990, 2, pp. 714-718.

M. B. Bornstein et al., "Clinical Trials of COP-1 in Multiple Sclerosis", *Handbook of Multiple Sclerosis*, S. D. Cook Marcel Rekker ed., 1990, pp. 469-480.

M. Wender, Copolymer 1 (COP-1) in the Treatment of Multiple Sclerosis (letter) *Neur. Neurochir. Pol.* (Poland), 1990, 24, pp. 113.

Z. Meiner, "COP-1 Multicenter Clinical Trial in Exacerbating-remitting Multiple-Sclerosis: one year follow-up", *J. of Neurol.*, 1991, supp 1. (abstract).

D. Teitelbaum et al., "Cross-reactions and Specificities of Monoclonal Antibodies Against Myelin Basic Protein and Against The synthetic, Copolymer 1." *Proc. Natl. Acad. Sci.*, (USA) 1991, 88, pp. 9528-9532.

M Salvetti et al., "Myelin Basic Protein T Cell Epitopes in Patients with Multiple Sclerosis", 72 (Abstract), 1991.

M. B. Bornstein et al., "Treatment of Multiple Sclerosis: Trial design, results and future Perspectives", Rudick R.K. & Goodkin D.E., eds. Springer Verlag, London, New York, 1992, pp. 173-198.

D. Teitelbaum et al., "Synthetic Copolymer 1 Inhibits Human T-Cell Lines Specific for Myelin Basic Protein", *Proc. Natl. Acad., Sci.*, (USA), 1992, 89, 137-141.

K. P. Johnson, "Clinical Studies in Copolymer 1 Therapy for Exacerbating-remitting Multiple Sclerosis", *Comm. presented at the Congress for Advances in the Understanding and Treatment of Multiple Sclerosis*, Boston (USA), Oct. 28-29, 1992.

R. Milo et al., "Inhibition of Myelin Basic Protein-Specific Human T-Cell Lines by COP-1", *Israel J. Med. Sci.*, 1992, 28, p. 486 (Abstract).

R. Arnon et al., "On the Existence of Suppressor Cells", Int. Arch. Allergy Immunol., 1993, 100, pp. 2-7.

M. Sela, "Polymeric Drugs as Immunomodulatory Vaccines Against Multiple Sclerosis", *Makromol. Chem. Macromol, Symp.*, 1993, 70/71, pp. 147-155.

Z. Meiner et al., "The Israeli COP-1 Multicenter Clinical Trial in Exacerbating-remitting Multiple Sclerosis two-year followup.", 9th Congress of the European Committee for Treatment and Research in Multiple Sclerosis, Florence (Italy), Oct.-Nov. 1993 Abstract.

R. Milo et al, "Copolymer-1 (COP-1) regulates class II MHC Expression and Cytokine Synthesis in the Monocyte-Macrophage Cell Line", *The IBC Conference on Multiple Sclerosis*, San Diego, Dec. 10, 1993 (Abstract).

M. Fridkis-Hareli et al., "Specific and Promiscuous Binding of Synthetic Copolymer-1 to Class II Major Histocompatibility Complex Molecules on Living Antigen Presenting Cells", *Israeli Biochemistry Society*, Mar. 1994 pp. 21-22 (Abstract).

M. Fridkis-Hareli et al., "Synthetic Copolymer-1 and Myelin Basic Protein do not Undergo Processing Prior to the Binding to Class II Major Histocompatibility Complex Molecules on Antigen Presenting Cells", *The Israeli Immunol. Soc.*, May 3-4, 1994 (Abstract).

R. Arnon et al., "Immunospecific Drug Design-Prospects for Treatment of Autoimmune Diseases", *Therapeutic Immunol.*, 1994, 1, pp. 65-70.

M. Fridkis-Hareli et al., "Synthetic Copolymer-1 Inhibits the Binding of MBP, PLP and MOG Peptides to Class II Major Histocompatibility Complex Molecules on Antigen Presenting Cells" *Neurochem Meeting*, Aug. 14-19, 1994.

Masha Fridkis-Hareli et al., "Synthetic Copolymer 1 and Myelin Basic Protein Do Not Require Processing Prior to Binding To Class II Major Histocompatibility Complex Molecules On Living Antigen Presenting Cells", *J. Neurochem*, 63, Suppl. 1, 561, 1994.

Kenneth P. Johnson, "Experimental Therapy of Relapsing-Remitting Multiple Sclerosis With Copolymer-1", *American Neurological Association*, 1994, 36, pp. 115-117.

E. Kott et al., "COP-1 Increases Suppressor Cells Number In Multiple Sclerosis", *Israel Neurological Association*, 1994, p. 17.

The COP-1 Multicenter Clinical and Research Group Study, "COP-1 Multicenter Trial in Relapsing Remitting Multiple Sclerosis: 3 Year Follow Up", *Abstracts of Symposia and Free Communications*, Jun. 25-29, 1994, suppl 1, 241, p. 6.

Yafit Stark, "Expanded Clinical Trials of Treatments for Multiple Sclerosis: Copolymer 1 Treatment Investigational New Drug Program", *Ann. Neurol*, 1994 36, pp. 114-115.

R. Milo et al., "Additive Effect of Copolymer-1 and Interferon-B on the Immune Response to Myelin Basic Protein", *Assaf Harofeh Medical Center, Sackler School of Medicine, Tel-Aviv University, Universty of Marland School of Medicine*, p. 22, 1994.

R. Milo et al., "Additive Effects of COP-1 and IFN-Beta on Immune Responses to Myelin Basic Protein", *Neurology*, 1994, 44, suppl. 2 A212.

D. Teitelbaum et al., "Immunological Parameters in a Multicenter Clinical Trial of COP1 in Multiple Sclerosis: A 2-year follow-up", *Neurology*, 1994 44, suppl. 2 A358.

M. Fridkis-Hareli et al., "Copolymer 1 Displaces MBP, PLP and MOG, but can not be displaced by these antigens from the MHC Class II binding Site", 1994.

Paul Cotton, "Options for Multiple Sclerosis Therapy", *JAMA Medical News & Perspectives*, 1994, 272, No. 18.

Lawrence Jacobs, "Advances in specific therapy for multiple sclerosis", *Neurology*, 1994, 7, pp. 250-254.

L. Durelli, "Immunotherapeutics of Multiple Sclerosis" pp. 467-475, 1994.

Lawrence Myers et al., "The Peculiar Difficulties of Therapeutic Trials for Multiple Sclerosis", *Neurologic Clinics*, Feb. 1990, 8, pp. 119-141.

D. A. Francis, "The Current Therapy of Multiple Sclerosis", *Journal of Clinical Pharmacy and Therapeutics*, 1993, 18, pp. 77-84.

Jonathan L. Carter et al., "Newer Drug Therapies for Multiple Sclerosis", Drug Therapy, Mar. 1990, pp. 31-43.

Brian G. Weinshenker et al., "Natural history and treatment of multiple sclerosis", *Current Opinion in Neurology and Neurosurgery*, 1992, 5, pp. 203-211.

Stuart Nightingale M.D. et al., "Access to Investigational Drugs for Treatment Purposes", *American Family Physician*, Sep. 15, 1994, pp. 845-847.

Shalini Bansil, M.D. et al., "Multiple Sclerosis: Pathogenesis and Treatment", *Seminars in Neurology*, Jun. 1994, 14, No. 2, pp. 146-153.

Masha Fridkis-Hareli et al., "Direct binding of myelin basic protein and synthetic copolymer 1 to class 11 major histocompatibility complex molecules on living antigen-presenting cells-specificity and promiscuity", *Proc. Natl, Acad. Sci.*, USA, May 1994, 91, pp. 4872-4876.

E. Gurevich, "Study of the MHC-competition between BP and Cop 1 using human cytotoxic T-cell clones" *Isr. J. Med. Sci*, 1993 (Abstract).

Masha Fridkis-Hareli et al., "Synthetic Copolymer 1 and Myelin Basic Protein do not require Processing prior to binding to class II major Histocompatibility Complex Molecules on Living Antigen Presenting Cells", Department of Chemical Immunology, The Weizmann Institute of Science, Rehovot, 76100, Israel; 1994.

Rolak, "Copolymer-I Therapy for Multiple Sclerosis," Dept. of Neurology, Baylor College of Medicine, Clinical Neuropharmacology, vol. 10, No. 5, pp. 389-396, Dec. 9, 1987.

M. Bodanszky, "Principles of Peptide Synthesis," Springer-Verlag, Berlin, Heidelberg, New York, Tokyo, 1984, 118-229.

J. Burris et al., "Failure of Copolymer 1 to Inhibit the Human T-cell Response to Myelin Basic Protein", *Neurology*, 41, pp. 1317-1319, 1991.

Clinical Trial Protocol No. 9001; first patient enrolled Oct. 23, 1991.

Clinical Trial Protocol No. 9002; first patient enrolled Jun. 17, 1993.

Idelson et al., "High Molecular Weight Poly-α, L-glutamic Acid: Preparation and Optical Rotation Changes," (1958) vol. 80, p. 4631-4364.

Ishai et al., "Cleavage of N-Carbobenzoxy Groups by Dry Hydrogen Bromide and Hydrogen Chloride," J. Org. Chem. (1952) vol. 17, p. 1564.

Sela, et al., "Multichain Polyamino Acids," J. Am. Chem. Soc. (1956) vol. 78, p. 746.

Pre-grant Opposition—Indian Patent Application No. 93/DEL/2003, dated Jan. 18, 2008.

* cited by examiner

COPOLYMER-1 IMPROVEMENTS IN COMPOSITIONS OF COPOLYMERS

This application is a continuation application of U.S. Ser. No. 11/098,432, filed Apr. 5, 2005 now U.S. Pat. No. 7,199,098, which is a continuation application of U.S. Ser. No. 10/615,865, filed Jul. 10, 2003, now U.S. Pat. No. 6,939,539, which is a continuation of application U.S. Ser. No. 10/014,477, filed Dec. 14, 2001, now U.S. Pat. No. 6,620,847, which is a continuation of application Ser. No. 09/510,466, filed Feb. 22, 2000, now U.S. Pat. No. 6,362,161, which is a continuation of U.S. Ser. No. 09/032,334 filed Feb. 27, 1998, now U.S. Pat. No. 6,048,898, which is a continuation of U.S. Ser. No. 08/447,146, filed May 22, 1995, now U.S. Pat. No. 5,800,808, which is a continuation-in-part of U.S. Ser. No. 08/344,248, filed Nov. 23, 1994, now abandoned, which is a continuation of U.S. Ser. No. 08/248,037, filed May 24, 1994, now abandoned.

BACKGROUND OF THE INVENTION

Copolymer-1 is a synthetic polypeptide analog of myelin basic protein (MBP), which is a natural component of the myelin sheath. It has been suggested as a potential therapeutic agent for multiple sclerosis (Eur. J. Immunol. [1971] 1:242; and J. Neurol. Sci. [1977]31:433. All references cited herein are hereby incorporated by reference in their entirety. Interest in copolymer-1 as an immunotherapy for multiple sclerosis stems from observations first made in the 1950's that myelin components such as MBP prevent or arrest experimental autoimmune encephalomyelitis (EAE). EAE is a disease resembling multiple sclerosis that can be induced in susceptible animals.

Copolymer-1 was developed by Drs. Sela, Arnon, and their co-workers at the Weizmann Institute (Rehovot, Israel). It was shown to suppress EAE (Eur. J. Immunol. [1971]1:242; U.S. Pat. No. 3,849,550). More recently, copolymer-1 was shown to be beneficial for patients with the exacerbating-remitting form of multiple sclerosis (N. Engl. J. Med. [1987] 317:408). Patients treated with daily injections of copolymer-1 had fewer exacerbations and smaller increases in their disability status than the control patients.

Copolymer-1 is a mixture of polypeptides composed of alanine, glutamic acid, lysine, and tyrosine in a molar ratio of approximately 6:2:5:1, respectively. It is synthesized by chemically polymerizing the four amino acids forming products with average molecular weights of 23,000 daltons (U.S. Pat. No. 3,849,550).

It is an object of the present invention to provide an improved composition of copolymer-1.

SUMMARY OF THE INVENTION

The present invention relates to a composition of copolymer-1 substantially free of species of copolymer-1 having a molecular weight of over 40 kilodaltons (KDa).

The invention further relates to a copolymer-1 having over 75% of its molar fraction within the molecular weight range from about 2 KDa to about 20 KDa.

In addition, the invention relates to a copolymer-1 having an average molecular weight of about 4 to about 8.6 KDa.

Moreover, the invention relates to a pharmaceutical composition and a method for the treatment of multiple sclerosis, using the above-discussed copolymer-1.

DETAILED DESCRIPTION OF THE INVENTION

Figure 1:
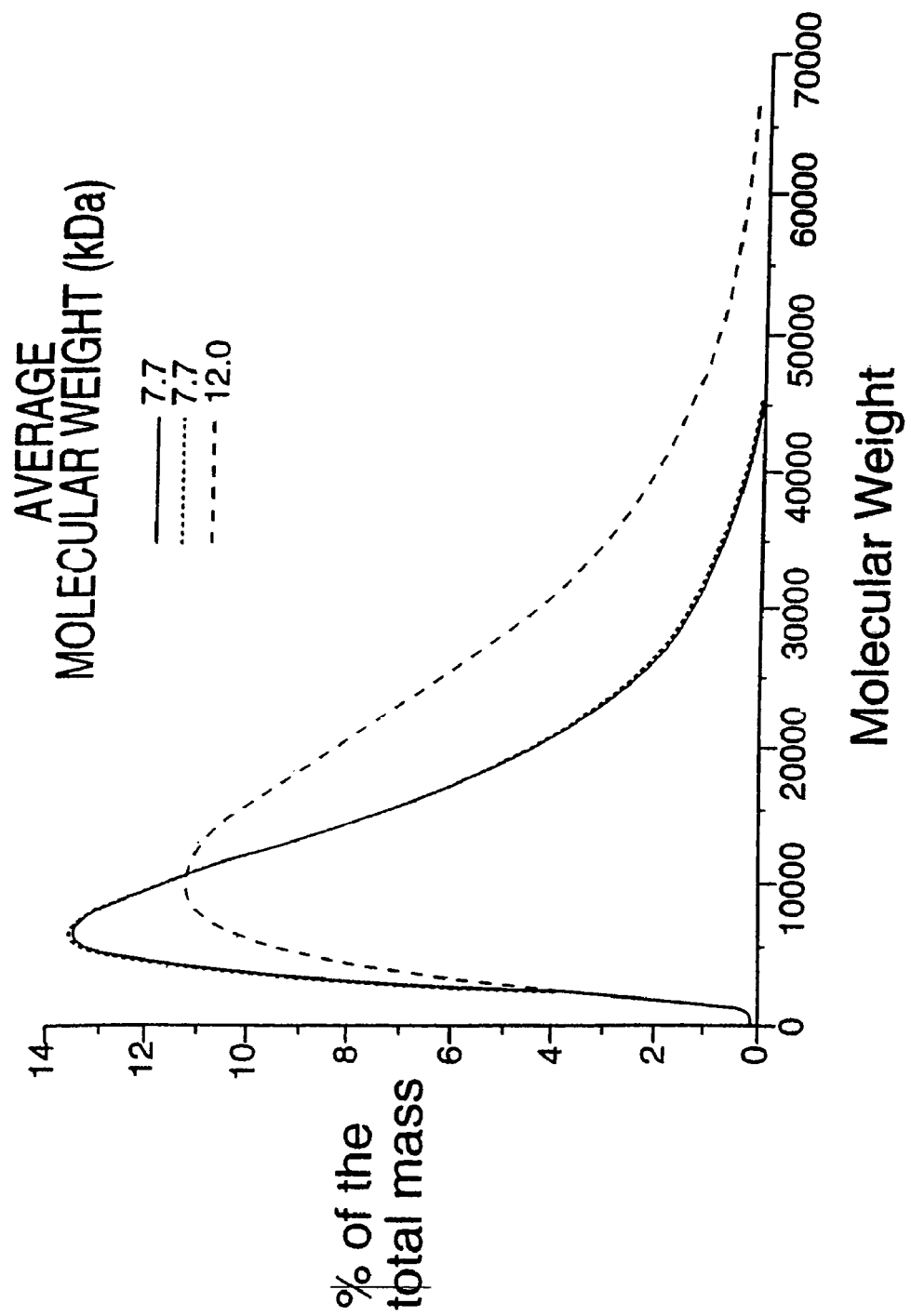
FIG. 1 displays the molecular weight distribution of three batches of copolymer-1, showing the proportion of species with molecular weight above 40 KDa.
Figure 2:
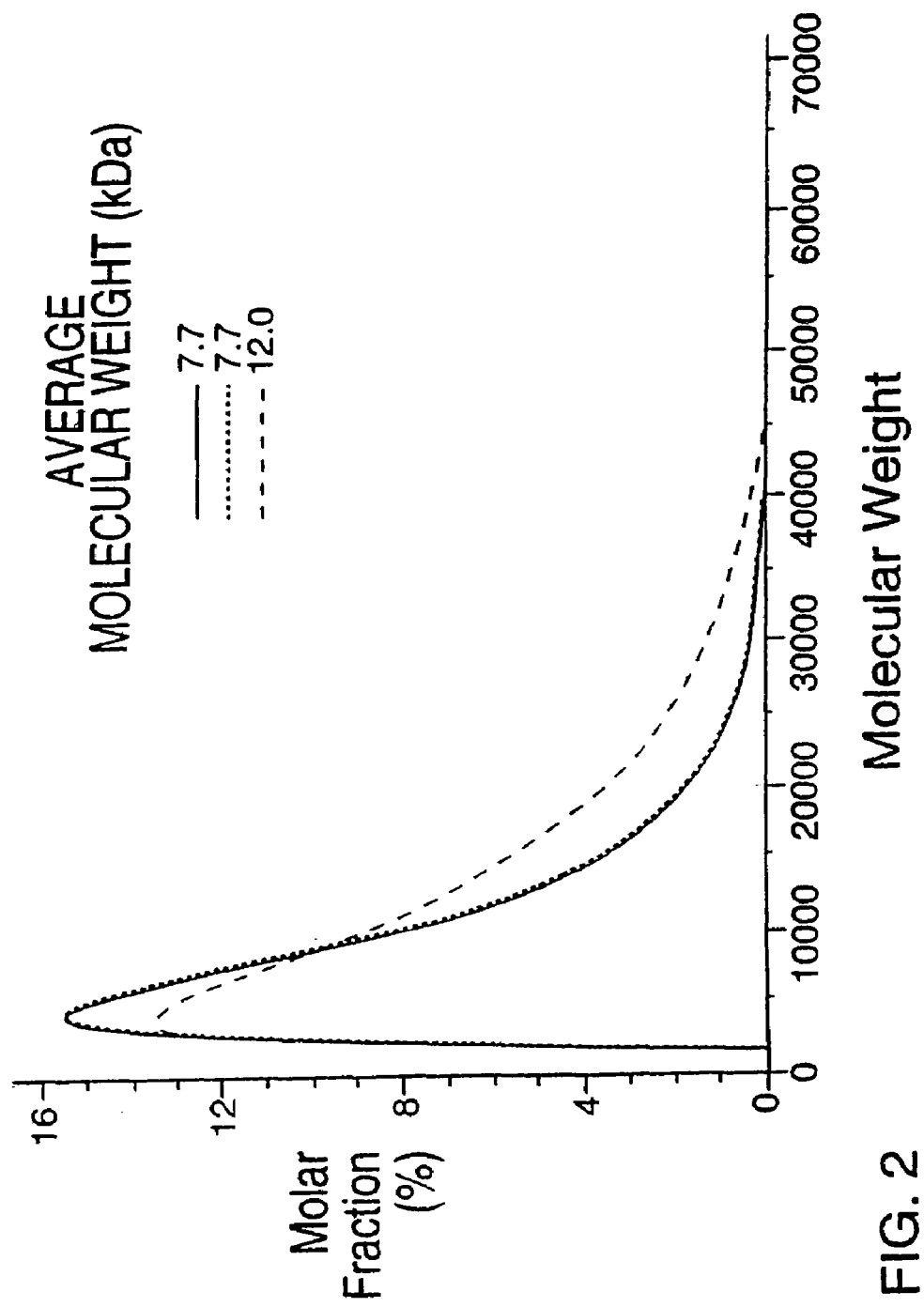
FIG. 2 shows similar data relating to the molar fraction.

The present invention relates to a composition of copolymer-1 substantially free of species of copolymer-1 having a molecular weight of over 40 kilodaltons (KDa). Preferably, the composition contains less than 5% of species of copolymer-1 having a molecular weight of 40 KDa or more. More preferably, the composition contains less than 2.5% of species of copolymer-1 having a molecular weight of 40 KDa, or more.

The invention further relates to a copolymer-1 having over 75% of its molar fraction within the molecular weight range from about 2 KDa to about 20 KDa.

In addition, the invention relates to a copolymer-1 having an average molecular weight of about 4 to about 8.6 KDa. In particular, the invention relates to a copolymer-1 having an average molecular weight of about 4 to about 8 KDa and a copolymer-1 having an average molecular weight of about 6.25 to about 8.4 KDa.

Copolymer-1, according to the present invention, may be prepared by methods known in the art, for example, the process disclosed in U.S. Pat. No. 3,849,550, wherein the N-carboxyanhydrides of tyrosine, alanine, y-benzyl glutamate and E-N-trifluoro-acetyllysine are polymerised at ambient temperature in anhydrous dioxane with diethylamine as initiator. The deblocking of the y-carboxyl group of the glutamic acid is effected by hydrogen bromide in glacial acetic acid and is followed by the removal of the trifluoroacetyl groups from the lysine residues by 1M piperidine. For the purposes of the application, the terms "ambient temperature" and "room temperature" should be understood to mean a temperature ranging from about 20 to about 26° C.

The copolymer-1 with the required molecular weight profile can be obtained either by methods known per se. Such methods include chromatography of copolymer-1 containing high molecular weight species and collecting the fractions without the undesired species or by partial acid or enzymatic hydrolysis to remove the high molecular weight species with subsequent purification by dialysis or ultrafiltration. A further method to obtain copolymer-1 with the desired molecular weight profile is by preparing the desired species while the amino acids are still protected and then obtain the correct species directly upon removing the protection. The compositions of the present invention may be formulated by conventional methods known in the art. Preferably, the composition is lyophilized and formed into an aqueous solution suitable for sub-cutaneous injection. Alternatively, copolymer-1 may be formulated in any of the forms known in the art for preparing oral, nasal, buccal, or rectal formulations of peptide drugs.

Typically, copolymer-1 is administered daily to patients suffering from multiple sclerosis at a dosage of 20 mg.

The invention will be exemplified but not necessarily limited by the following Examples.

Example 1

Chromatographic Method of Preparation of Low-Toxicity Copolymer-1

Two batches of copolymer-1 were prepared according to the methods known in the art, for example, U.S. Pat. No. 3,849,550.

One batch was then subjected to chromatographic separation, as described below.

A column for gel filtration, FRACTOGEL TSK HW55 (600×26 mm) was prepared in a Superformance 26 Merck cartridge according to the manufacturer's instructions. The column as equilibrated with water and acetone solution was injected for total volume determination. The column was quilibrated with 0.2M ammonium acetate buffer pH 5.0. 30 ml copolymer-1 samples (20 mg/ml, in 0.2M ammonium cetate pH 5.0) were loaded on the column and fractions ere collected every 10 minutes. A fraction having an average molecular weight of 7-8 KDa was isolated between 120-130 minutes (Batch A).

Molecular Weight Analysis

UV absorbance at 275 nm was determined in a UVIKON 810 spectrophotometer. Samples were diluted to obtain a UV absorbance lower than 1 Absorption Unit. The molecular distribution of the 2 batches was determined on a calibrated gel filtration column (Superose 12).

Copolymer-1 batch A was found to have an average molecular weight of 7-8 KDa. 2.5% of this batch had a molecular weight above 32 KDa, but no copolymer-1 species present in this batch had a molecular weight of over 40 KDa.

The other batch of copolymer-1 which was not subjected to chromatography, had an average molecular weight of 12 KDa. 2.5% of the batch had a molecular weight above 42 KDa and 5% of the total copolymer-1 species in this batch had a molecular weight of over 40 KDa.

Example 2

Toxicity Analysis

A: In Vivo

Three batches of copolymer-1 having an average molecular weight of 7.3 and 8.4 KDa (less than 2.5% copolymer-1 species over 40 KDa) and 22 KDa (more than 5% copolymer-1 species over 40 KDa) were subjected to the toxicity test described below. In each case 5 mice were used in each experimental group.

Method

Copolymer-1 was dissolved in distilled water to yield a solution of 2 mg/ml of the active ingredient. Each mouse was injected with 0.5 ml of the test solution into the lateral tail vein. Mice were observed for mortality and relevant clinical signs over a 48 hour period. Observations were recorded 10 minutes, 24 hours and 48 hours post-injection. If, at the end of 48 hours, all the animals were alive and no adverse signs had been observed, then the batch was designated "non-toxic". If, however, one or more of the mice had died or had shown adverse signs, then the batch was designated "toxic".

The batches with the average molecular weight of 7.3 and 8.4 KDa were both designated "non-toxic", whereas in the batch with the average molecular weight of 22 KDa, 3 out of 5 mice had died at the end of 48 hours, and it was consequently designated "toxic".

B: In Vitro

RBL—Degranulation Test

I. Introduction

Histamine (or serotonin) release from basophile is an in vitro model for immediate hypersensitivity. The Rat Basophilic Leukemia cell line (RBL-$2H_3$) was developed and characterized as a highly sensitive, uniform, easy to maintain in culture and reproducible system (E. L. Basumian, C. Isersky, M. G. Petrino and R. P. Siraganian. Eur. J. Immunol. 11, 317 (1981)). The physiological stimulus for histamine release involves binding of the antigen to membrane-bound IgE molecules, resulting in the latter's cross-linking and the consequent triggering of an intricate biochemical cascade. Beside these physiological, immunoglobulin-mediated triggers, degranulation can be induced by different non-IgE-mediated stimuli. Among these are various peptides and synthetic polymers, e.g. polylysine (R. P. Siraganian. rends in Pharmacological Sciences, October 432 (1983)). The RBL degranulation test is, therefore, used in order to screen out those batches of copolymer-1 which evoke substantial degranulation and thus might elicit undesirable local and/or systemic side effects.

II. Principle of the Test Method

Rat Basophilic Leukemia cells (RBL-$2H_3$), are loaded with [$^3$H]-serotonin, followed by incubation with 100 μg of the copolymer-1 to be tested. Batches of copolymer-1 which induce non-specific degranulation, release [$^3$H]-serotonin into the medium. The radioactivity in the medium is counted by a scintillation counter and the total radiolabeled serotonin incorporated into the cells is determined in the pelleted cells. Percent degranulation is calculated as the percentage of serotonin released out of the total incorporated.

III. Results

Four batches of copolymer-1, with average molecular weight between 6,250-14,500 were analyzed for both % of the species with molecular weight over 40 KDa and for degranulation of RBL's. Results are summarized in the following table.

| Average M.W. (Daltons) | % of species with M.W. over 40 KDa | % Serotonin Release |
|---|---|---|
| 6,250 | <2.5 | 12.4 |
| 7,300 | <2.5 | 21.0 |
| 13,000 | >5 | 66.9 |
| 14,500 | >5 | 67.8 |

As can be seen, when the % of high molecular weight species is low (<2.5), the % release of serotonin, indicative of toxicity, is low, and vice versa.

Example 3

Preparation of Trifluoroacetyl-Copolymer-1

Protected copolymer-1 is prepared as described by Teitelbaum et al. Eur. J. Immun. Vol. 1 p. 242 (1971) from the N-carboxyanhydrides of tyrosine (18 g), alanine (50 g), γ-benzyl glutamate (35 g) and tritluoroacetyllysine (83 g) dissolved in 3.5 liters of dioxane.

The polymerization process is initiated by the addition of 0.01-0.02% diethylamine. The reaction mixture is stirred at room temperature for 24 hours and then poured into 10 liters water. The product (protected copolymer-1) is filtered, washed with water and dried. The removal of the gamma-benzyl blocking groups from the glutamate residue is carried out by treating the protected copolymer-1 with 33% hydrobromic acid in glacial acetic acid at room temperature for 6-12 hours with stirring. The product is poured into excess water, filtered, washed and dried, yielding the trifluoroacetyl-copolymer-1.

Example 4

Preparation of Trifluoroacetyl-Copolymer-1

Protected copolymer-1 is prepared as described by Teitelbaum et al. Eur. J. Immun. Vol. 1 p. 242 (1971) from the N-carboxyanhydrides of tyrosine (18 g), alanine (50 g), τ-benzyl glutamate (35 g) and trifluoroacetyllysine (83 g) dissolved in 3.5 liters of dioxane.

The polymerization process is initiated by the addition of 0.01-0.02% diethylamine. The reaction mixture is stirred at room temperature for 24 hours and then poured into 10 liters water. The product (protected copolymer-1) is filtered, washed with water and dried.

Protected copolymer-1 is treated with 33% HBr in acetic acid which removes the omega benzyl protecting group from the 5-carboxylate of the glutamate residue and cleaves the polymer to smaller polypeptides. The time needed for obtaining copolymer-1 of molecular weight 7,000±2,000 Da depends on the reaction temperature and the size of protected copolymer-1. At temperatures of between 20-28° C. a test reaction is performed on every batch at different time periods for example, from 10-50 hours.

The results concerning the molecular weights of these small scale reactions are calculated and a curve of molecular weight against time is drawn. The time needed for obtaining molecular weight 7,000±2,000 Da is calculated from the curve and performed on larger scale reaction. On average, working at 26° C. the time period is 17 hours. The product is poured into excess water, filtered, washed and dried, yielding the trifluoroacetyl-copolymer-1.

Preparation of Low-Toxicity Copolymer-1

20 g of trifluoroacetyl-copolymer-1 are dispersed in 1 liter of water to which 100 g piperidine are added. The mixture is stirred for 24 hours at room temperature and filtered. The solution of crude copolymer-1 is distributed into dialysis bags and dialyzed at 10°-20° C. against water until a pH=8 is attained. It is then dialyzed against about 0.3% acetic acid and again water until a pH=5.5-6.0 is obtained. This solution is then concentrated and lyophilized to dryness.

The invention claimed is:

1. A process for preparing a copolymer-1 composition having a target average molecular weight comprising:
    providing a first copolymer-1 composition having an average molecular weight greater than the target average molecular weight;
    removing a sufficient amount of copolymer species having a molecular weight greater than the target average molecular weight to obtain a second copolymer-1 composition having the target average molecular weight;
    wherein the target average molecular weight falls within the range of about 4 to about 8.6 kDa.

2. The process of claim 1, wherein the number of copolymer species having a molecular weight greater than 40 kDa in the second copolymer-1 composition is less than half the number of copolymer species having a molecular weight greater than 40 kDa in the first copolymer-1 composition.

3. The process of claim 1, further comprising isolating the second copolymer-1 composition.

4. The process of claim 1, wherein the removing of copolymer species having a molecular weight greater than the target average molecular weight comprises physically separating copolymer species having a molecular weight greater than the target average molecular weight.

5. The process of claim 4, wherein the physically separating step comprises chromatographic separation.

6. The process of claim 1, wherein the removing of copolymer species having a molecular weight greater than the target average molecular weight comprises cleaving copolymer species having a molecular weight greater than the target average molecular weight.

7. The process of claim 5, wherein the cleaving step comprises acid hydrolysis.

8. The process of claim 6, further comprising isolating the second copolymer-1 composition by dialysis or ultrafiltration of the result of the cleaving step.

9. The process of claim 5, wherein the cleaving step comprises enzymatic hydrolysis.

10. The process of claim 8, further comprising isolating the second copolymer-1 composition by dialysis or ultrafiltration of the result of the cleaving step.

11. The process of claim 5, further comprising isolating the second copolymer-1 composition by dialysis or ultrafiltration of the result of the cleaving step.

* * * * *